(12) United States Patent
Doyle et al.

(10) Patent No.: US 8,676,285 B2
(45) Date of Patent: Mar. 18, 2014

(54) METHODS FOR VALIDATING PATIENT IDENTITY

(75) Inventors: Peter Doyle, Vista, CA (US); Joseph Douglas Vandine, Manteca, CA (US); Warren Sanborn, Escondido, CA (US); Dan Graboi, Encinitas, CA (US)

(73) Assignee: Covidien LP, Mansfield, MA (US)

( * ) Notice: Subject to any disclaimer, the term of this patent is extended or adjusted under 35 U.S.C. 154(b) by 887 days.

(21) Appl. No.: 12/844,942

(22) Filed: Jul. 28, 2010

(65) Prior Publication Data

US 2012/0029317 A1  Feb. 2, 2012

(51) Int. Cl.
*G03B 41/00* (2006.01)

(52) U.S. Cl.
USPC ........................................................ 600/323

(58) Field of Classification Search
USPC ........................................................ 396/323
See application file for complete search history.

(56) References Cited

U.S. PATENT DOCUMENTS

| | | |
|---|---|---|
| 3,805,780 A | 4/1974 | Cramer et al. |
| 3,941,124 A | 3/1976 | Rodewald et al. |
| 4,056,098 A | 11/1977 | Michel et al. |
| 4,305,388 A | 12/1981 | Brisson |
| 4,340,044 A | 7/1982 | Levy et al. |
| 4,752,089 A | 6/1988 | Carter |
| 4,921,642 A | 5/1990 | LaTorraca |
| 4,939,647 A | 7/1990 | Clough et al. |
| 4,954,799 A | 9/1990 | Kumar |
| 4,971,052 A | 11/1990 | Edwards |
| 4,986,268 A | 1/1991 | Tehrani |
| 5,057,822 A | 10/1991 | Hoffman |
| 5,072,737 A | 12/1991 | Goulding |
| 5,094,235 A | 3/1992 | Westenskow et al. |
| 5,150,291 A | 9/1992 | Cummings et al. |
| 5,161,525 A | 11/1992 | Kimm et al. |
| 5,237,987 A | 8/1993 | Anderson et al. |
| 5,271,389 A | 12/1993 | Isaza et al. |
| 5,279,549 A | 1/1994 | Ranford |
| 5,299,568 A | 4/1994 | Forare et al. |
| 5,301,921 A | 4/1994 | Kumar |
| 5,315,989 A | 5/1994 | Tobia |
| 5,319,540 A | 6/1994 | Isaza et al. |
| 5,325,861 A | 7/1994 | Goulding |
| 5,333,606 A | 8/1994 | Schneider et al. |
| 5,339,807 A | 8/1994 | Carter |
| 5,343,857 A | 9/1994 | Schneider et al. |
| 5,351,522 A | 10/1994 | Lura |
| 5,357,946 A | 10/1994 | Kee et al. |
| 5,365,922 A | 11/1994 | Raemer |

(Continued)

FOREIGN PATENT DOCUMENTS

| | | |
|---|---|---|
| WO | WO2004000114 | 12/2003 |
| WO | WO2007145948 | 12/2007 |

OTHER PUBLICATIONS

7200 Series Ventilator, Options, and Accessories: Operator's Manual. Nellcor Puritan Bennett, Part No. 22300 A, Sep. 1990, pp. 1-196.

(Continued)

*Primary Examiner* — Rodney Fuller

(57) ABSTRACT

This disclosure describes systems and methods for monitoring a patient on a ventilator-oximeter system. The disclosure describes a novel approach determining if the oximeter and the ventilator are attached to the same patient and if not providing a warning.

23 Claims, 6 Drawing Sheets

(56) References Cited

U.S. PATENT DOCUMENTS

| | | |
|---|---|---|
| 5,368,019 A | 11/1994 | LaTorraca |
| 5,383,449 A | 1/1995 | Forare et al. |
| 5,385,142 A | 1/1995 | Brady et al. |
| 5,388,575 A | 2/1995 | Taube |
| 5,390,666 A | 2/1995 | Kimm et al. |
| 5,398,682 A | 3/1995 | Lynn |
| 5,401,135 A | 3/1995 | Stoen et al. |
| 5,402,796 A | 4/1995 | Packer et al. |
| 5,407,174 A | 4/1995 | Kumar |
| 5,413,110 A | 5/1995 | Cummings et al. |
| 5,429,123 A | 7/1995 | Shaffer et al. |
| 5,438,980 A | 8/1995 | Phillips |
| 5,443,075 A | 8/1995 | Holscher |
| 5,503,147 A | 4/1996 | Bertheau |
| 5,513,631 A | 5/1996 | McWilliams |
| 5,517,983 A | 5/1996 | Deighan et al. |
| 5,520,071 A | 5/1996 | Jones |
| 5,524,615 A | 6/1996 | Power |
| 5,531,221 A | 7/1996 | Power |
| 5,535,738 A | 7/1996 | Estes et al. |
| 5,540,220 A | 7/1996 | Gropper et al. |
| 5,542,415 A | 8/1996 | Brady |
| 5,544,674 A | 8/1996 | Kelly |
| 5,549,106 A | 8/1996 | Gruenke et al. |
| 5,551,419 A | 9/1996 | Froehlich et al. |
| 5,596,984 A | 1/1997 | O'Mahoney et al. |
| 5,605,151 A | 2/1997 | Lynn |
| 5,623,923 A | 4/1997 | Bertheau et al. |
| 5,630,411 A | 5/1997 | Holscher |
| 5,632,270 A | 5/1997 | O'Mahoney et al. |
| 5,645,048 A | 7/1997 | Brodsky et al. |
| 5,660,171 A | 8/1997 | Kimm et al. |
| 5,664,560 A | 9/1997 | Merrick et al. |
| 5,664,562 A | 9/1997 | Bourdon |
| 5,671,767 A | 9/1997 | Kelly |
| 5,672,041 A | 9/1997 | Ringdahl et al. |
| 5,673,689 A | 10/1997 | Power |
| 5,692,497 A | 12/1997 | Schnitzer et al. |
| 5,715,812 A | 2/1998 | Deighan et al. |
| 5,762,480 A | 6/1998 | Adahan |
| 5,771,884 A | 6/1998 | Yarnall et al. |
| 5,791,339 A | 8/1998 | Winter |
| 5,794,986 A | 8/1998 | Gansel et al. |
| 5,813,399 A | 9/1998 | Isaza et al. |
| 5,826,575 A | 10/1998 | Lall |
| 5,829,441 A | 11/1998 | Kidd et al. |
| 5,864,938 A | 2/1999 | Gansel et al. |
| 5,865,168 A | 2/1999 | Isaza |
| 5,881,717 A | 3/1999 | Isaza |
| 5,881,723 A | 3/1999 | Wallace et al. |
| 5,884,623 A | 3/1999 | Winter |
| 5,891,023 A | 4/1999 | Lynn |
| 5,909,731 A | 6/1999 | O'Mahony et al. |
| 5,915,379 A | 6/1999 | Wallace et al. |
| 5,915,380 A | 6/1999 | Wallace et al. |
| 5,915,382 A | 6/1999 | Power |
| 5,918,597 A | 7/1999 | Jones et al. |
| 5,921,238 A | 7/1999 | Bourdon |
| 5,934,274 A | 8/1999 | Merrick et al. |
| 6,024,089 A | 2/2000 | Wallace et al. |
| 6,041,780 A | 3/2000 | Richard et al. |
| 6,047,860 A | 4/2000 | Sanders |
| 6,076,523 A | 6/2000 | Jones et al. |
| 6,116,240 A | 9/2000 | Merrick et al. |
| 6,116,464 A | 9/2000 | Sanders |
| 6,123,073 A | 9/2000 | Schlawin et al. |
| 6,123,074 A | 9/2000 | Hete et al. |
| 6,135,106 A | 10/2000 | Dirks et al. |
| 6,142,150 A | 11/2000 | O'Mahony et al. |
| 6,148,814 A | 11/2000 | Clemmer et al. |
| 6,158,430 A | 12/2000 | Pfeiffer et al. |
| 6,158,432 A | 12/2000 | Biondi et al. |
| 6,159,147 A | 12/2000 | Lichter et al. |
| 6,161,539 A | 12/2000 | Winter |
| 6,220,245 B1 | 4/2001 | Takabayashi et al. |
| 6,223,064 B1 | 4/2001 | Lynn et al. |
| 6,269,812 B1 | 8/2001 | Wallace et al. |
| 6,273,444 B1 | 8/2001 | Power |
| 6,283,119 B1 | 9/2001 | Bourdon |
| 6,305,373 B1 | 10/2001 | Wallace et al. |
| 6,321,748 B1 | 11/2001 | O'Mahoney |
| 6,325,785 B1 | 12/2001 | Babkes et al. |
| 6,342,039 B1 | 1/2002 | Lynn et al. |
| 6,357,438 B1 | 3/2002 | Hansen |
| 6,360,745 B1 | 3/2002 | Wallace et al. |
| 6,369,838 B1 | 4/2002 | Wallace et al. |
| 6,371,114 B1 | 4/2002 | Schmidt et al. |
| 6,390,091 B1 | 5/2002 | Banner et al. |
| 6,412,483 B1 | 7/2002 | Jones et al. |
| 6,439,229 B1 | 8/2002 | Du et al. |
| 6,467,478 B1 | 10/2002 | Merrick et al. |
| 6,512,938 B2 | 1/2003 | Claure et al. |
| 6,532,958 B1 | 3/2003 | Buan et al. |
| 6,532,959 B1 | 3/2003 | Berthon-Jones |
| 6,532,960 B1 | 3/2003 | Yurko |
| 6,536,429 B1 | 3/2003 | Pavlov et al. |
| 6,543,449 B1 | 4/2003 | Woodring et al. |
| 6,546,930 B1 | 4/2003 | Emerson et al. |
| 6,553,991 B1 | 4/2003 | Isaza |
| 6,557,553 B1 | 5/2003 | Borrello |
| 6,561,187 B2 | 5/2003 | Schmidt et al. |
| 6,571,795 B2 | 6/2003 | Bourdon |
| 6,602,191 B2 | 8/2003 | Quy |
| 6,609,016 B1 | 8/2003 | Lynn |
| 6,622,726 B1 | 9/2003 | Du |
| 6,640,806 B2 | 11/2003 | Yurko |
| 6,644,310 B1 | 11/2003 | Delache et al. |
| 6,644,312 B2 | 11/2003 | Berthon-Jones et al. |
| 6,665,385 B2 | 12/2003 | Rogers et al. |
| 6,668,824 B1 | 12/2003 | Isaza et al. |
| 6,671,529 B2 | 12/2003 | Claure et al. |
| 6,675,801 B2 | 1/2004 | Wallace et al. |
| 6,688,307 B2 | 2/2004 | Berthon-Jones |
| 6,718,974 B1 | 4/2004 | Moberg |
| 6,723,055 B2 | 4/2004 | Hoffman |
| 6,725,447 B1 | 4/2004 | Gilman et al. |
| 6,739,337 B2 | 5/2004 | Isaza |
| 6,748,252 B2 | 6/2004 | Lynn et al. |
| 6,752,151 B2 | 6/2004 | Hill |
| 6,758,216 B1 | 7/2004 | Berthon-Jones et al. |
| 6,760,608 B2 | 7/2004 | Lynn |
| 6,761,165 B2 | 7/2004 | Strickland |
| 6,761,167 B2 | 7/2004 | Nadjafizadeh et al. |
| 6,761,168 B1 | 7/2004 | Nadjafizadeh et al. |
| 6,796,305 B1 | 9/2004 | Banner et al. |
| 6,814,074 B1 | 11/2004 | Nadjafizadeh et al. |
| 6,820,618 B2 | 11/2004 | Banner et al. |
| 6,837,242 B2 | 1/2005 | Younes |
| 6,866,040 B1 | 3/2005 | Bourdon |
| 6,868,346 B2 | 3/2005 | Larson et al. |
| 6,960,854 B2 | 11/2005 | Nadjafizadeh et al. |
| 7,008,380 B1 | 3/2006 | Rees et al. |
| 7,036,504 B2 | 5/2006 | Wallace et al. |
| 7,066,173 B2 | 6/2006 | Banner et al. |
| 7,077,131 B2 | 7/2006 | Hansen |
| 7,081,095 B2 | 7/2006 | Lynn et al. |
| RE39,225 E | 8/2006 | Isaza et al. |
| 7,089,936 B2 | 8/2006 | Madaus et al. |
| 7,092,376 B2 | 8/2006 | Schuman |
| 7,092,757 B2 | 8/2006 | Larson et al. |
| 7,100,609 B2 | 9/2006 | Berthon-Jones et al. |
| 7,117,438 B2 | 10/2006 | Wallace et al. |
| 7,152,598 B2 | 12/2006 | Morris et al. |
| 7,210,478 B2 | 5/2007 | Banner et al. |
| 7,229,430 B2 | 6/2007 | Hickle et al. |
| 7,267,122 B2 | 9/2007 | Hill |
| 7,270,126 B2 | 9/2007 | Wallace et al. |
| 7,275,540 B2 | 10/2007 | Bolam et al. |
| 7,296,573 B2 | 11/2007 | Estes et al. |
| 7,297,119 B2 | 11/2007 | Westbrook et al. |
| 7,315,535 B2 | 1/2008 | Schuman |
| 7,331,343 B2 | 2/2008 | Schmidt et al. |
| 7,353,824 B1 | 4/2008 | Forsyth et al. |
| 7,369,757 B2 | 5/2008 | Farbarik |

(56) References Cited

U.S. PATENT DOCUMENTS

| | | |
|---|---|---|
| 7,370,650 B2 | 5/2008 | Nadjafizadeh et al. |
| 7,398,115 B2 | 7/2008 | Lynn |
| 7,406,870 B2 | 8/2008 | Seto |
| 7,428,902 B2 | 9/2008 | Du et al. |
| 7,448,381 B2 | 11/2008 | Sasaki et al. |
| 7,455,583 B2 | 11/2008 | Taya |
| 7,460,959 B2 | 12/2008 | Jafari |
| 7,487,773 B2 | 2/2009 | Li |
| 7,509,957 B2 | 3/2009 | Duquette et al. |
| 7,590,551 B2 | 9/2009 | Auer |
| 7,654,802 B2 | 2/2010 | Crawford, Jr. et al. |
| 7,694,677 B2 | 4/2010 | Tang |
| 7,698,156 B2 | 4/2010 | Martucci et al. |
| 7,715,387 B2 | 5/2010 | Schuman |
| 7,717,113 B2 | 5/2010 | Andrieux |
| D618,356 S | 6/2010 | Ross |
| 7,784,461 B2 | 8/2010 | Figueiredo et al. |
| 7,823,588 B2 | 11/2010 | Hansen |
| 7,855,716 B2 | 12/2010 | McCreary et al. |
| D632,796 S | 2/2011 | Ross et al. |
| D632,797 S | 2/2011 | Ross et al. |
| 7,891,354 B2 | 2/2011 | Farbarik |
| 7,893,560 B2 | 2/2011 | Carter |
| D638,852 S | 5/2011 | Skidmore et al. |
| 7,984,714 B2 | 7/2011 | Hausmann et al. |
| D643,535 S | 8/2011 | Ross et al. |
| 7,992,557 B2 | 8/2011 | Nadjafizadeh et al. |
| 8,001,967 B2 | 8/2011 | Wallace et al. |
| D645,158 S | 9/2011 | Sanchez et al. |
| 8,021,310 B2 | 9/2011 | Sanborn et al. |
| D649,157 S | 11/2011 | Skidmore et al. |
| D653,749 S | 2/2012 | Winter et al. |
| 8,113,062 B2 | 2/2012 | Graboi et al. |
| D655,405 S | 3/2012 | Winter et al. |
| D655,809 S | 3/2012 | Winter et al. |
| 8,181,648 B2 | 5/2012 | Perine et al. |
| 8,210,173 B2 | 7/2012 | Vandine |
| 8,210,174 B2 | 7/2012 | Farbarik |
| 8,240,684 B2 | 8/2012 | Ross et al. |
| 8,267,085 B2 | 9/2012 | Jafari et al. |
| 8,272,379 B2 | 9/2012 | Jafari et al. |
| 8,272,380 B2 | 9/2012 | Jafari et al. |
| 8,302,600 B2 | 11/2012 | Andrieux et al. |
| 8,302,602 B2 | 11/2012 | Andrieux et al. |
| 2002/0133061 A1 | 9/2002 | Manetta |
| 2002/0185126 A1 | 12/2002 | Krebs |
| 2003/0158466 A1 | 8/2003 | Lynn et al. |
| 2003/0221689 A1 | 12/2003 | Berthon-Jones |
| 2005/0039748 A1 | 2/2005 | Andrieux |
| 2005/0109340 A1 | 5/2005 | Tehrani |
| 2005/0133027 A1 | 6/2005 | Elaz et al. |
| 2005/0139212 A1 | 6/2005 | Bourdon |
| 2005/0172965 A1 | 8/2005 | Thulin |
| 2006/0112959 A1 | 6/2006 | Mechlenburg et al. |
| 2006/0155206 A1 | 7/2006 | Lynn |
| 2006/0155207 A1 | 7/2006 | Lynn et al. |
| 2006/0161071 A1 | 7/2006 | Lynn et al. |
| 2006/0189880 A1 | 8/2006 | Lynn et al. |
| 2006/0195041 A1 | 8/2006 | Lynn et al. |
| 2006/0235324 A1 | 10/2006 | Lynn |
| 2006/0241708 A1 | 10/2006 | Boute |
| 2006/0264762 A1 | 11/2006 | Starr |
| 2006/0272642 A1 | 12/2006 | Chalvignac |
| 2007/0000494 A1* | 1/2007 | Banner et al. ............ 128/204.23 |
| 2007/0016441 A1 | 1/2007 | Stroup |
| 2007/0017515 A1 | 1/2007 | Wallace et al. |
| 2007/0027375 A1 | 2/2007 | Melker et al. |
| 2007/0028921 A1 | 2/2007 | Banner et al. |
| 2007/0072541 A1 | 3/2007 | Daniels, II et al. |
| 2007/0077200 A1 | 4/2007 | Baker |
| 2007/0093721 A1 | 4/2007 | Lynn et al. |
| 2007/0129647 A1 | 6/2007 | Lynn |
| 2007/0149860 A1 | 6/2007 | Lynn et al. |
| 2007/0157931 A1 | 7/2007 | Parker et al. |
| 2007/0163579 A1 | 7/2007 | Li et al. |
| 2007/0185390 A1 | 8/2007 | Perkins et al. |
| 2007/0191688 A1 | 8/2007 | Lynn |
| 2007/0191697 A1* | 8/2007 | Lynn et al. ............ 600/323 |
| 2007/0215154 A1 | 9/2007 | Borrello |
| 2007/0227537 A1 | 10/2007 | Bemister et al. |
| 2007/0272241 A1 | 11/2007 | Sanborn et al. |
| 2007/0277823 A1 | 12/2007 | Al-Ali et al. |
| 2007/0284361 A1 | 12/2007 | Nadjafizadeh et al. |
| 2008/0000479 A1 | 1/2008 | Elaz et al. |
| 2008/0053441 A1 | 3/2008 | Gottlib et al. |
| 2008/0066752 A1 | 3/2008 | Baker et al. |
| 2008/0066753 A1 | 3/2008 | Martin et al. |
| 2008/0072896 A1 | 3/2008 | Setzer et al. |
| 2008/0072902 A1 | 3/2008 | Setzer et al. |
| 2008/0078390 A1 | 4/2008 | Milne et al. |
| 2008/0081974 A1 | 4/2008 | Pav |
| 2008/0083644 A1 | 4/2008 | Janbakhsh et al. |
| 2008/0092894 A1 | 4/2008 | Nicolazzi et al. |
| 2008/0097234 A1 | 4/2008 | Nicolazzi et al. |
| 2008/0110460 A1 | 5/2008 | Elaz et al. |
| 2008/0178880 A1 | 7/2008 | Christopher et al. |
| 2008/0178882 A1 | 7/2008 | Christopher et al. |
| 2008/0200775 A1 | 8/2008 | Lynn |
| 2008/0200819 A1 | 8/2008 | Lynn et al. |
| 2008/0251079 A1 | 10/2008 | Richey |
| 2009/0165795 A1 | 7/2009 | Nadjafizadeh et al. |
| 2009/0171176 A1 | 7/2009 | Andersohn |
| 2009/0171226 A1 | 7/2009 | Campbell et al. |
| 2009/0205661 A1 | 8/2009 | Stephenson et al. |
| 2009/0205663 A1 | 8/2009 | Vandine et al. |
| 2009/0241952 A1 | 10/2009 | Nicolazzi et al. |
| 2009/0241953 A1 | 10/2009 | Vandine et al. |
| 2009/0241956 A1 | 10/2009 | Baker, Jr. et al. |
| 2009/0241957 A1 | 10/2009 | Baker, Jr. |
| 2009/0241958 A1 | 10/2009 | Baker, Jr. |
| 2009/0241962 A1 | 10/2009 | Jafari et al. |
| 2009/0247891 A1 | 10/2009 | Wood |
| 2009/0301486 A1 | 12/2009 | Masic |
| 2009/0301487 A1 | 12/2009 | Masic |
| 2009/0301490 A1 | 12/2009 | Masic |
| 2009/0301491 A1 | 12/2009 | Masic et al. |
| 2010/0011307 A1 | 1/2010 | Desfossez et al. |
| 2010/0024820 A1 | 2/2010 | Bourdon |
| 2010/0051026 A1 | 3/2010 | Graboi |
| 2010/0051029 A1 | 3/2010 | Jafari et al. |
| 2010/0069761 A1 | 3/2010 | Karst et al. |
| 2010/0071689 A1 | 3/2010 | Thiessen |
| 2010/0071692 A1 | 3/2010 | Porges |
| 2010/0071695 A1 | 3/2010 | Thiessen |
| 2010/0071696 A1 | 3/2010 | Jafari |
| 2010/0071697 A1 | 3/2010 | Jafari et al. |
| 2010/0078017 A1 | 4/2010 | Andrieux et al. |
| 2010/0078026 A1 | 4/2010 | Andrieux et al. |
| 2010/0081119 A1 | 4/2010 | Jafari et al. |
| 2010/0081955 A1 | 4/2010 | Wood, Jr. et al. |
| 2010/0139660 A1 | 6/2010 | Adahan |
| 2010/0147303 A1 | 6/2010 | Jafari et al. |
| 2010/0186744 A1 | 7/2010 | Andrieux |
| 2010/0218765 A1 | 9/2010 | Jafari et al. |
| 2010/0218766 A1 | 9/2010 | Milne |
| 2010/0218767 A1 | 9/2010 | Jafari et al. |
| 2010/0236555 A1 | 9/2010 | Jafari et al. |
| 2010/0242961 A1 | 9/2010 | Mougel et al. |
| 2010/0282259 A1 | 11/2010 | Figueiredo et al. |
| 2010/0288283 A1 | 11/2010 | Campbell et al. |
| 2010/0300446 A1 | 12/2010 | Nicolazzi et al. |
| 2011/0011400 A1 | 1/2011 | Gentner et al. |
| 2011/0023878 A1 | 2/2011 | Thiessen |
| 2011/0023879 A1 | 2/2011 | Vandine et al. |
| 2011/0023880 A1 | 2/2011 | Thiessen |
| 2011/0023881 A1 | 2/2011 | Thiessen |
| 2011/0029910 A1 | 2/2011 | Thiessen |
| 2011/0041849 A1 | 2/2011 | Chen et al. |
| 2011/0041850 A1 | 2/2011 | Vandine et al. |
| 2011/0126829 A1 | 6/2011 | Carter et al. |
| 2011/0126832 A1 | 6/2011 | Winter et al. |
| 2011/0126834 A1 | 6/2011 | Winter et al. |
| 2011/0126835 A1 | 6/2011 | Winter et al. |
| 2011/0126836 A1 | 6/2011 | Winter et al. |

(56) References Cited

U.S. PATENT DOCUMENTS

| | | |
|---|---|---|
| 2011/0126837 A1 | 6/2011 | Winter et al. |
| 2011/0128008 A1 | 6/2011 | Carter |
| 2011/0132361 A1 | 6/2011 | Sanchez |
| 2011/0132362 A1 | 6/2011 | Sanchez |
| 2011/0132364 A1 | 6/2011 | Ogilvie et al. |
| 2011/0132365 A1 | 6/2011 | Patel et al. |
| 2011/0132366 A1 | 6/2011 | Ogilvie et al. |
| 2011/0132367 A1 | 6/2011 | Patel |
| 2011/0132368 A1 | 6/2011 | Sanchez et al. |
| 2011/0132369 A1 | 6/2011 | Sanchez |
| 2011/0132371 A1 | 6/2011 | Sanchez et al. |
| 2011/0133936 A1 | 6/2011 | Sanchez et al. |
| 2011/0138308 A1 | 6/2011 | Palmer et al. |
| 2011/0138309 A1 | 6/2011 | Skidmore et al. |
| 2011/0138311 A1 | 6/2011 | Palmer |
| 2011/0138315 A1 | 6/2011 | Vandine et al. |
| 2011/0138323 A1 | 6/2011 | Skidmore et al. |
| 2011/0146681 A1 | 6/2011 | Jafari et al. |
| 2011/0146683 A1 | 6/2011 | Jafari et al. |
| 2011/0175728 A1 | 7/2011 | Baker, Jr. |
| 2011/0196251 A1 | 8/2011 | Jourdain et al. |
| 2011/0209702 A1 | 9/2011 | Vuong et al. |
| 2011/0209704 A1 | 9/2011 | Jafari et al. |
| 2011/0209707 A1 | 9/2011 | Terhark |
| 2011/0213215 A1 | 9/2011 | Doyle et al. |
| 2011/0259330 A1 | 10/2011 | Jafari et al. |
| 2011/0259332 A1 | 10/2011 | Sanchez et al. |
| 2011/0259333 A1 | 10/2011 | Sanchez et al. |
| 2011/0265024 A1 | 10/2011 | Leone et al. |
| 2011/0271960 A1 | 11/2011 | Milne et al. |
| 2011/0273299 A1 | 11/2011 | Milne et al. |
| 2012/0000467 A1 | 1/2012 | Milne et al. |
| 2012/0000468 A1 | 1/2012 | Milne et al. |
| 2012/0000469 A1 | 1/2012 | Milne et al. |
| 2012/0000470 A1 | 1/2012 | Milne et al. |
| 2012/0030611 A1 | 2/2012 | Skidmore |
| 2012/0041279 A1* | 2/2012 | Freeman et al. ............ 600/301 |
| 2012/0071729 A1* | 3/2012 | Doyle et al. ............... 600/301 |
| 2012/0090611 A1* | 4/2012 | Graboi et al. ............ 128/204.23 |
| 2012/0136222 A1* | 5/2012 | Doyle et al. ............... 600/301 |
| 2013/0025597 A1* | 1/2013 | Doyle et al. ............ 128/204.23 |

OTHER PUBLICATIONS

7200 Ventilatory System: Addendum/Errata. Nellcor Puritan Bennett, Part No. 4-023576-00, Rev. A, Apr. 1998, pp. 1-32.

800 Operator's and Technical Reference Manual. Series Ventilator System, Nellcor Puritan Bennett, Part No. 4-070088-00, Rev. L, Aug. 2010, pp. 1-476.

840 Operator's and Technical Reference Manual. Ventilator System, Nellcor Puritan Bennett, Part No. 4-075609-00, Rev. G, Oct. 2006, pp. 1-424.

* cited by examiner

METHODS FOR VALIDATING PATIENT IDENTITY

Medical ventilator systems have been long used to provide supplemental oxygen support to patients. These ventilators typically include a source of pressurized oxygen which is fluidly connected to the patient through a conduit. In some systems, the proper arterial oxygen saturation ($SpO_2$) is monitored via a pulse oximeter attached to the patient.

A pulse oximeter includes a light sensor that is placed at a site on a patient, usually a fingertip, toe, forehead or earlobe, or in the case of a neonate, across a foot. Light, which may be produced by a light source integrated into the pulse oximeter, containing both red and infrared wavelengths is directed onto the skin of the patient and the light that passes through the skin is detected by the sensor. The intensity of light in each wavelength is measured by the sensor over time. The graph of light intensity versus time is referred to as the photoplethysmogram (PPG) or, more commonly, simply as the "pleth." From the waveform of the PPG, it is possible to identify the pulse rate of the patient and when each individual pulse occurs. In addition, by comparing the intensities of two wavelengths when a pulse occurs, it is possible to determine blood oxygen saturation of hemoglobin in arterial blood. This relies on the observation that highly oxygenated blood will relatively absorb more red light and less infrared light than blood with a lower oxygen saturation.

Ventilators and oximeters are often used in combination on patients during ventilation. The oximeter and ventilator may be operatively coupled, but each system, regardless of coupling, is attached to a patient separately. Coupling allows the systems to communicate readings to each other. On occasion, the oximeter sensor is placed on a patient who is not the same as the ventilator patient even though the oximeter and ventilator are both supposed to be attached the same patient. Additionally, on occasion, the oximeter sensor is not attached to a patient at all. In these cases, the ventilation parameters may be changed based on inaccurate data hindering proper patient treatment.

SUMMARY

This disclosure describes systems and methods for monitoring a patient on a ventilator-oximeter system. The disclosure describes a novel approach determining if the oximeter and the ventilator are attached to the same patient and if not providing a warning.

In part, this disclosure describes a method for monitoring a patient being ventilated by a medical ventilator-oximeter system including:

a) monitoring at least one patient parameter using data gathered by an oximeter;

b) monitoring the same at least one patient parameter from data gathered by a ventilator independently of the oximeter;

c) comparing the at least one patient parameter monitored by the oximeter to the same at least one patient parameter monitored by the ventilator; and d) executing an alarm to notify an operator of the medical ventilator-oximeter system that an oximeter sensor is not attached to the patient being ventilated by the ventilator when the at least one patient parameter monitored by the oximeter and the ventilator differ by more than a predetermined value.

Another aspect of this disclosure describes a method for monitoring a patient being ventilated by a medical ventilator-oximeter system including:

a) monitoring a pulse rate of a patient using data gathered by an oximeter;

b) monitoring the pulse rate of the patient using data gathered by a ventilator independently of the oximeter;

c) comparing the pulse rate monitored by the oximeter to the pulse rate monitored by the ventilator; and d) executing an alarm to notify an operator of the medical ventilator-oximeter system that an oximeter sensor is not attached to the patient being ventilated by the ventilator when the pulse rate monitored by the oximeter and the pulse rate monitored by the ventilator differ by more than a predetermined value.

Yet another aspect of this disclosure describes a method for monitoring a patient being ventilated by a medical ventilator-oximeter system including:

a) monitoring a respiration rate of a patient using data gathered from an oximeter;

b) monitoring the respiration rate of the patient using data gathered by a ventilator independently of the oximeter;

c) comparing the respiration rate monitored by the oximeter to the respiration rate monitored by the ventilator; and d) executing an alarm to notify an operator of the medical ventilator-oximeter system that an oximeter sensor is not attached to the patient being ventilated by the ventilator when the respiration rate monitored by the oximeter and the respiration rate monitored by the ventilator differ by more than a predetermined value.

The disclosure further describes a medical ventilator-oximeter system. The medical ventilator-oximeter system includes:

a) a ventilator, the ventilator including a processor, a pneumatic gas delivery system controlled by the processor, the pneumatic gas delivery system adapted to control a flow of gas from a gas supply to a patient via a ventilator breathing circuit, at least one sensor in communication with the processor, data from the at least one sensor is utilized to determine a respiration rate of the patient, and a cardiac oscillation detector in communication with the processor, data from the cardiac oscillation detector is utilized to determine a pulse rate of the patient;

b) an oximeter operatively coupled to the ventilator, the oximeter includes an oximeter sensor in communication with the processor, a pulse rate module in communication with the processor, and an infrared plethysmorgram module in communication with the processor;

c) a comparing module, the comparing module compares at least one patient parameter monitored by using oximeter data to the same at least one patient parameter monitored by using ventilator data gathered independently of the oximeter data;

d) an alarm module, the alarm module executes an alarm when the at least one patient parameter monitored by using the oximeter data and the same at least one patient parameter monitored by using the ventilator data differ by more than a predetermined value; and e) a display module controlled by the processor, the display module is adapted to display an executed alarm Yet another aspect of this disclosure describes a computer-readable medium having computer-executable instructions for performing a method for monitoring a patient being ventilated by a medical ventilator-oximeter system. The method includes:

a) repeatedly monitoring at least one patient parameter with an oximeter and with a ventilator independently of the oximeter;

b) repeatedly comparing the at least one patient parameter monitored by the oximeter to the at least one patient parameter monitored by the ventilator;

c) determining that the at least one patient parameter monitored by the oximeter differs from the at least one parameter monitored by the ventilator by more than a predetermined value; and d) executing an alarm after the step of determining that the at least one patient parameter monitored by the oximeter differs from the at least one parameter monitored by the ventilator by more than a predetermined value.

A further aspect of this disclosure describes a medical ventilator-oximeter system including means for repeatedly monitoring at least one patient parameter with an oximeter and with a ventilator independently of the oximeter, means for repeatedly comparing the at least one patient parameter monitored by the oximeter to the at least one patient parameter monitored by the ventilator, means for determining that the at least one patient parameter monitored by the oximeter differs from the at least one parameter monitored by the ventilator by more than a predetermined value, and means for executing an alarm after the step of determining that the at least one patient parameter monitored by the oximeter differs from the at least one parameter monitored by the ventilator by more than a predetermined value.

These and various other features as well as advantages which characterize the systems and methods described herein will be apparent from a reading of the following detailed description and a review of the associated drawings. Additional features are set forth in the description which follows, and in part will be apparent from the description, or may be learned by practice of the technology. The benefits and features of the technology will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

The following drawing figures, which form a part of this application, are illustrative of embodiment systems and methods described below and are not meant to limit the scope of the invention in any manner, which scope shall be based on the claims appended hereto.

DETAILED DESCRIPTION

Figure 1:
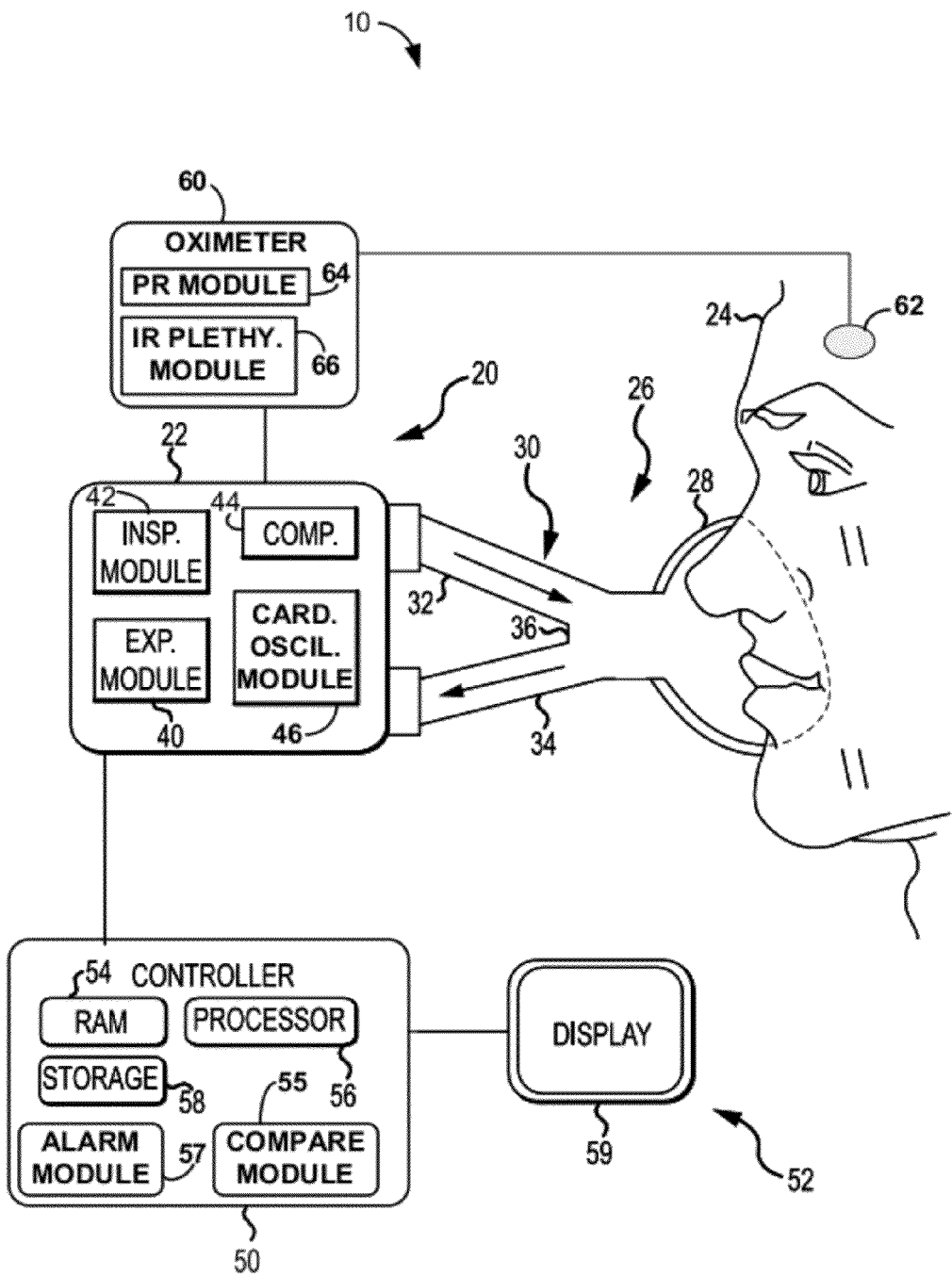
FIG. 1 illustrates an embodiment of a ventilator-oximeter system connected to a human patient.

Although the techniques introduced above and discussed in detail below may be implemented for a variety of medical devices, the present disclosure will discuss the implementation of these techniques in the context of a medical ventilator for use in providing ventilation support to a human patient. The reader will understand that the technology described in the context of a medical ventilator for human patients could be adapted for use with other systems such as ventilators for non-human patients and general gas transport systems.

Medical ventilators are used to provide a breathing gas to a patient who may otherwise be unable to breathe sufficiently. In modern medical facilities, pressurized air and oxygen sources are often available from wall outlets. However, ventilators may also provide pressure regulating valves (or regulators) connected to localized sources of pressurized air and pressurized oxygen. Internal to the ventilator are regulating valves that function to regulate flow so that respiratory gas having a desired concentration of oxygen is supplied to the patient at desired pressures and rates. Ventilators capable of operating independently of external sources of pressurized air are also available.

While operating a ventilator, it is desirable to control the percentage of oxygen in the gas supplied by the ventilator to the patient. Further, it is desirable to monitor the oxygen saturation level of blood ($SpO_2$ level) of a patient. Accordingly, systems typically have oximeters for non-invasively measuring the $SpO_2$ level of a patient.

The oximeter and ventilator can be operatively coupled, but each system, regardless of coupling, is attached to the patient separately. Coupling allows the systems to communicate readings to each other. On occasion, the oximeter sensor is placed on the wrong patient or not on the ventilator patient. Additionally, on occasion, the oximeter sensor is not attached to a patient at all. In these instances, ventilator readings, settings, and/or warnings can be based on inaccurate data and hinder proper patient treatment. Prior ventilation systems provided no safeguards for these mistakes. Therefore, it is desirable to provide an automated system that can detect when a ventilator and oximeter are not attached to the same patient. Accordingly, the medical ventilator-oximeter system disclosed herein can determine if the oximeter and ventilator are attached to the same patient and if not, provide for an appropriate warning.

The ventilator-oximeter system disclosed herein includes a ventilator operatively coupled to an oximeter. The ventilator-oximeter system disclosed herein utilizes at least one common patient parameter monitored from data gathered by the ventilator and from data gathered independently by the oximeter to determine if the ventilator and oximeter are attached to the same patient. Further, the ventilator-oximeter system may utilize the same plurality of patient parameters monitored from data gathered by the ventilator and from data gathered independently by the oximeter to determine if the ventilator and oximeter are attached to the same patient In one embodiment, the ventilator-oximeter system compares independently determined pulse rates of a patient. In this embodiment the oximeter, via its specific sensor, monitors the pulse rate of a patient. Concurrently, the ventilator monitors cardiac oscillations to derive the pulse rate of the patient independently from the oximeter. The ventilator and/or oximeter compares the pulse rate calculated by the oximeter and the ventilator. If the difference between the two measurements exceeds a predetermined threshold, the ventilator and/or oximeter executes a warning notifying the operator that the oximeter is not attached to the same patient as the ventilator. If the pulse rate measurements are similar enough, the ventilator and/or oximeter does not execute an alarm because the ventilator and the oximeter are most likely attached to the same patient. Additionally, the phase of the independently measured pulse rates may be compared. Similarly, if the pulse rate phase measurements differ by more than a predetermined value or threshold, the ventilator and/or oximeter executes a warning notifying the operator that the oximeter is not attached to the same patient as the ventilator.

In another embodiment, the ventilator-oximeter system compares independently determined respiration rates of the patient. In this embodiment, the oximeter receives oximeter data, such as an IR plethysmogram baseline modulation, to monitor the respiration rate and/or actual positive pressure output of the patient. Concurrently, the ventilator independently monitors the respiration rate and/or actual positive pressure output of the patient from received ventilator-gathered data. The ventilator may monitor the respiration rate of the patient by monitoring data received from ventilator sensors, such as a flow sensor or pressure sensor, or the ventilator may know the respiration rate of the patient because the rate is set by ventilator parameters. The ventilator and/or oximeter compares the respiration rate monitored by the oximeter with the respiration rate monitored by the ventilator. If the rates are too different to have been taken from the same patient, the ventilator and/or oximeter executes a warning or an alarm notifying the operator that the oximeter is not attached to the same patient as the ventilator. If the respiration rate measurements are similar enough, the ventilator and/or oximeter does not execute an alarm because the ventilator and the oximeter are most likely attached to the same patient. Additionally, the phase duration of the independently measured respiration rates may be compared. If the respiration rate phase durations differ by more than a predetermined threshold or value, the ventilator and/or oximeter executes a warning notifying the operator that the oximeter is not attached to the same patient as the ventilator.

In a further embodiment, the ventilator-oximeter compares independently determined respiration rates and pulse rates of the patient. The combination of the two patient parameters provides for a more robust implementation of this safety check. In this embodiment, the oximeter data are utilized calculate pulse rate and the ventilation system data are utilized to determine the frequency of cardiac oscillations (if present) on the ventilation pressure waveform to calculate pulse rate. Next, the oximeter and/or ventilator compares the calculated pulse rates. Concurrently, in this embodiment, the ventilator monitors the frequency of pressure excursion in the ventilation pressure waveform and the oximeter monitors the frequency of changes in the magnitude of modulation (max-min) of the infrared (IR) plethysmorgram and/or baseline light level (a.k.a. the "DC" component). The oximeter and/or the ventilator then compares these frequencies. If either comparison shows a frequency difference (particularly the same frequency difference, if a difference is detected in both) that is greater than a predetermined value, an alarm is issued by the ventilator and/or oximeter. If both comparisons show no frequency difference or a difference that is equal to or less than a predetermined value, an alarm is not issued by the ventilator and/or oximeter because the ventilator and the oximeter are most likely attached to the same patient. The predetermined value, is the value of difference necessary for determining that the patient parameters were not calculated from sensor measurements taken from the same patient Those skilled in the art will recognize that the methods and systems of the present disclosure may be implemented in many manners and as such are not to be limited by the foregoing exemplary embodiments and examples. In other words, functional elements being performed by a single or multiple components, in various combinations of hardware and software or firmware, and individual functions, can be distributed among software applications at either the client or server level or both. In this regard, any number of the features of the different embodiments described herein may be combined into single or multiple embodiments, and alternate embodiments having fewer than or more than all of the features herein described are possible. Functionality may also be, in whole or in part, distributed among multiple components, in manners now known or to become known. Thus, myriad software/hardware/firmware combinations are possible in achieving the functions, features, interfaces and preferences described herein. Moreover, the scope of the present disclosure covers conventionally known manners for carrying out the described features and functions and interfaces, and those variations and modifications that may be made to the hardware or software or firmware components described herein as would be understood by those skilled in the art now and hereafter.

Unless otherwise indicated, all numbers expressing quantities, properties, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present disclosure.

FIG. 1 illustrates an embodiment of a ventilator-oximeter system 10 attached to a human patient 24. The ventilator-oximeter system 10 includes a ventilator system 20 operatively coupled to an oximeter system 60. The ventilator system 20 and the oximeter system 60 are each separately attached to a patient 24. To prevent the oximeter system 60 from being attached to the wrong patient or no patient at all, the ventilator-oximeter system 10 determines if the oximeter system 60 is attached to patient 24 being ventilated by ventilator system 20 and if not, provides an alarm.

Ventilator system 20 includes a pneumatic system 22 (also referred to as a pressure generating system 22) for circulating breathing gases to and from patient 24 via the ventilation tubing system 26, which couples the patient 24 to the pneumatic system 22 via physical patient interface 28 and ventilator circuit 30.

Ventilator circuit 30 could be a two-limb or one-limb circuit 30 for carrying gas to and from the patient 24. In a two-limb embodiment as shown, a wye fitting 36 may be provided as shown to couple the patient interface 28 to the inspiratory limb 32 and the expiratory limb 34 of the circuit 30. Examples of suitable patient interfaces 28 include a nasal mask, nasal/oral mask (which is shown in FIG. 1), nasal prong, full-face mask, tracheal tube, endotracheal tube, nasal pillow, etc.

Pneumatic system 22 may be configured in a variety of ways. In the present example, system 22 includes an expiratory module 40 coupled with an expiratory limb 34 and an inspiratory module 42 coupled with an inspiratory limb 32. Compressor 44 or another source or sources of pressurized gas (e.g., pressured air and/or oxygen) is controlled through the use of one or more pneumatic gas delivery systems.

As shown, in one embodiment, the pneumatic system 22 further includes a cardiac oscillation module 46. In an alternative embodiment, the cardiac oscillation module 46 is located within another component of ventilator system 20. The cardiac oscillation module 46 detects small pressure (flow) fluctuations in the breathing circuit that originate in the lungs-thorax of patient 24 as a result of the systolic-diastolic action of the heart. These fluctuations allow the cardiac oscillation module 46 of ventilator system 20 to determine the pulse rate of patient 24 being ventilated.

The pneumatic system 22 may include a variety of other components, including sources for pressurized air and/or oxygen, mixing modules, valves, sensors, tubing, filters, etc.

The oximeter system 60 of the ventilator-oximeter system 10 measures an oxygen saturation level of blood in a patient ($SpO_2$) attached to an oximeter sensor 62. The oximeter system 60 is operatively coupled to the oximeter sensor 62.

As shown, in one embodiment, the oximeter system 60 is a completely separate and independent component from ventilator system 20. In an alternative embodiment, oximeter system 60 is located inside of ventilator system 20 and/or the pneumatic system 22. As discussed above, the oximeter system 60 and the ventilator system 20 are operatively coupled. This coupling allows the ventilator system 20 and the oximeter system 60 to communicate with each other.

In one embodiment, the oximeter system 60 includes a pulse rate module 64 and/or an infrared (IR) plethysmorgram module 66. The pulse rate module 64 derives the pulse rate of the patient attached to the oximeter sensor 62 by monitoring signal bounces in time caused by the expansion and contraction of the arterial blood vessels with each heartbeat. The infrared (IR) plethysmorgram module 66 detects the frequency of changes in the magnitude of modulation (max-min) of the IR plethysmorgram and/or baseline light level (a.k.a. the "DC" component) to determine the respiration rate or the actual positive pressure output of the patient attached to the oximeter sensor 62. In an alternative embodiment, the data gathered by the pulse rate module 64 and/or the infrared (IR) plethysmorgram module 66 is sent to the ventilator and ventilator calculates the oximeter pulse rate and oximeter respiration rate of the patient from oximeter gathered data.

Controller 50 is operatively coupled with pneumatic system 22, oximeter system 60, signal measurement and acquisition systems, and an operator interface 52, which may be provided to enable an operator to interact with the ventilator system 20 (e.g., change ventilator settings, select operational modes, view monitored parameters, etc.). Controller 50 may include memory 54, one or more processors 56, storage 58, and/or other components of the type commonly found in command and control computing devices. In one embodiment, controller 50 further includes a compare module 55 and/or an alarm module 57.

The processor 56 is the logic circuitry that responds to and processes instructions that drive a computer. Examples of processors include general-purpose microprocessors, application specific integrated circuits (ASICs) and field programmable gate arrays (FPGAs).

The memory 54 is non-transitory computer-readable storage media that stores software that is executed by the processor 56 and which controls the operation of the ventilator system 20. In an embodiment, the memory 54 includes one or more solid-state storage devices such as flash memory chips. In an alternative embodiment, the memory 54 may be mass storage connected to the processor 56 through a mass storage controller (not shown) and a communications bus (not shown). Although the description of non-transitory computer-readable media contained herein refers to a solid-state storage, it should be appreciated by those skilled in the art that non-transitory computer-readable storage media can be any available media that can be accessed by the processor 56. Non-transitory computer-readable storage media includes volatile and non-volatile, removable and non-removable media implemented in any method or technology for storage of information such as non-transitory computer-readable instructions, data structures, program modules or other data. Non-transitory computer-readable storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the processor 56.

The compare module 55 of controller 50 compares at least one patient parameter measured from data gathered by the oximeter system 60 with the same at least one patient parameter measured from data gathered by the ventilator system 20. In one embodiment, compare module 55 is activated upon user or operator command. In an alternative embodiment, the compare module 55 is activated based on a preset, a preconfigured, or a preselected ventilator setting. In another embodiment, compare module 55 is activated repeatedly based on a preset, a preconfigured, or a preselected ventilator setting. In one embodiment, compare module 55 compares the pulse rate calculated form data gathered by oximeter system 60 with the pulse rate determined independently from data gathered by ventilator system 20. In another embodiment, compare module 55 compares the respiration rate calculated from data gathered by oximeter system 60 with the respiration rate determined independently from data gathered by ventilator system 20. In an alternative embodiment, compare module 55 compares the pulse rate and respiration rate calculated from data gathered by oximeter system 60 with the pulse rate and respiration rate determined independently from data gathered by ventilator system 20.

The alarm module 57 of controller 50 determines if the compared patient parameters determined from data gathered by oximeter system 60 and data gathered from the ventilator system 20 differ by more than a predetermined value. In one embodiment, the predetermined value is selected by an operator or inputted by an operator. In another embodiment the predetermined value is about 5% to about 10%. This range is not limiting. The predetermined value may vary depending upon the patient and the ventilator application. In one embodiment, the predetermined value is about 5%. Accordingly, alarm module 57 considers the patient parameters similar enough to be calculated from sensor readings from the same patient if the readings are about 95% or more equivalent. In one embodiment, the compared patient parameters are at least one of pulse rate and respiration rate.

If the alarm module 57 determines that any of the patient parameters measured independently from data gathered by ventilator system 20 and oximeter system 60 differ by more than a predetermined value, alarm module 57 executes an alarm. The alarm may be an audio and/or visual warning. The visual warning may include flashing lights, a designated icon, or a simple worded notice on the display screen. This list is not limiting. Any suitable visual warning for notifying a ventilator-oximeter system operator that oximeter sensor 62 is not attached to patient 24 being ventilated by ventilator system 20 may be utilized by the ventilator-oximeter system 10. If the alarm module 57 determines that the patient parameters determined independently from data gathered by ventilator system 20 and oximeter system 60 are equal to or less than the predetermined value, alarm module 57 does nothing because it is likely that oximeter sensor 62 is attached to patient 24 being ventilated by ventilator system 20.

The warning or alarm alerts the operator that the oximeter sensor 62 should be checked and if oximeter sensor 62 is not on patient 24, oximeter sensor 62 should be placed on patient 24. Accordingly, the alarm provides the operator of the ventilator system 20 with a check for verifying that the oximeter sensor 62 of oximeter system 60 is attached to ventilation patient 24 to prevent the ventilator-oximeter system 10 from displaying incorrect information based on improper oximeter information. Further, the alarm provides the operator of the ventilator system 20 with a check for verifying that the oximeter system 60 and the ventilator system 20 are performing properly and/or not processing corrupted data. This check helps to prevent the operator from improperly treating patient 24 based on the improper information.

The controller 50 further issues commands to pneumatic system 22 in order to control the breathing assistance provided to patient 24 by ventilator system 20. The specific commands may be based on data inputs received from patient 24, pneumatic system 22, sensors, operator interface 52, oximeter system 60, and/or other components of the ventilator system 20.

In the depicted example, operator interface 52 includes a display 59 that is touch-sensitive, enabling the display 59 to serve both as an input user interface and an output device. In an alternative embodiment, the display 59 is not touch sensitive or an input user interface. The display 59 can display any type of ventilation information, such as sensor readings, parameters, commands, alarms, warnings, and/or smart prompts (i.e., ventilator determined operator suggestions). In one embodiment, display 59 displays an alarm notifying a ventilator-oximeter system operator that the oximeter sensor 62 is not attached to patient 24 being ventilated by ventilator system 20.

In the embodiment shown in FIG. 1, oximeter system 60 does not include an oximeter controller. In an alternative embodiment, oximeter system 60 includes an oximeter controller. The oximeter controller is operatively coupled with pneumatic system 22, signal measurement and acquisition systems, controller 50, operator interface 52, and/or display 59. The oximeter controller may include memory, one or more processors, storage, and/or other components of the type commonly found in command and control computing devices. In one embodiment, the oximeter controller further includes a compare module and an alarm module. In another embodiment, the oximeter controller includes a compare module and an alarm module and the ventilator controller 50 does not include these modules.

The memory of the oximeter controller is non-transitory computer-readable storage media that stores software that is executed by the processor and which controls the operation of the ventilator. In an embodiment, the memory includes one or more solid-state storage devices such as flash memory chips. In an alternative embodiment, the memory may be mass storage connected to the processor through a mass storage controller (not shown) and a communications bus (not shown). Although the description of non-transitory computer-readable media contained herein refers to a solid-state storage, it should be appreciated by those skilled in the art that non-transitory computer-readable storage media can be any available media that can be accessed by the processor. Non-transitory computer-readable storage media includes volatile and non-volatile, removable and non-removable media implemented in any method or technology for storage of information such as non-transitory computer-readable instructions, data structures, program modules or other data. Non-transitory computer-readable storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the processor.

The compare module of the oximeter controller performs all the same function as discussed above for compare module 55 of controller 50. The alarm module of the oximeter controller performs all the same function as discussed above for alarm module 57 of controller 50.

Figure 2:
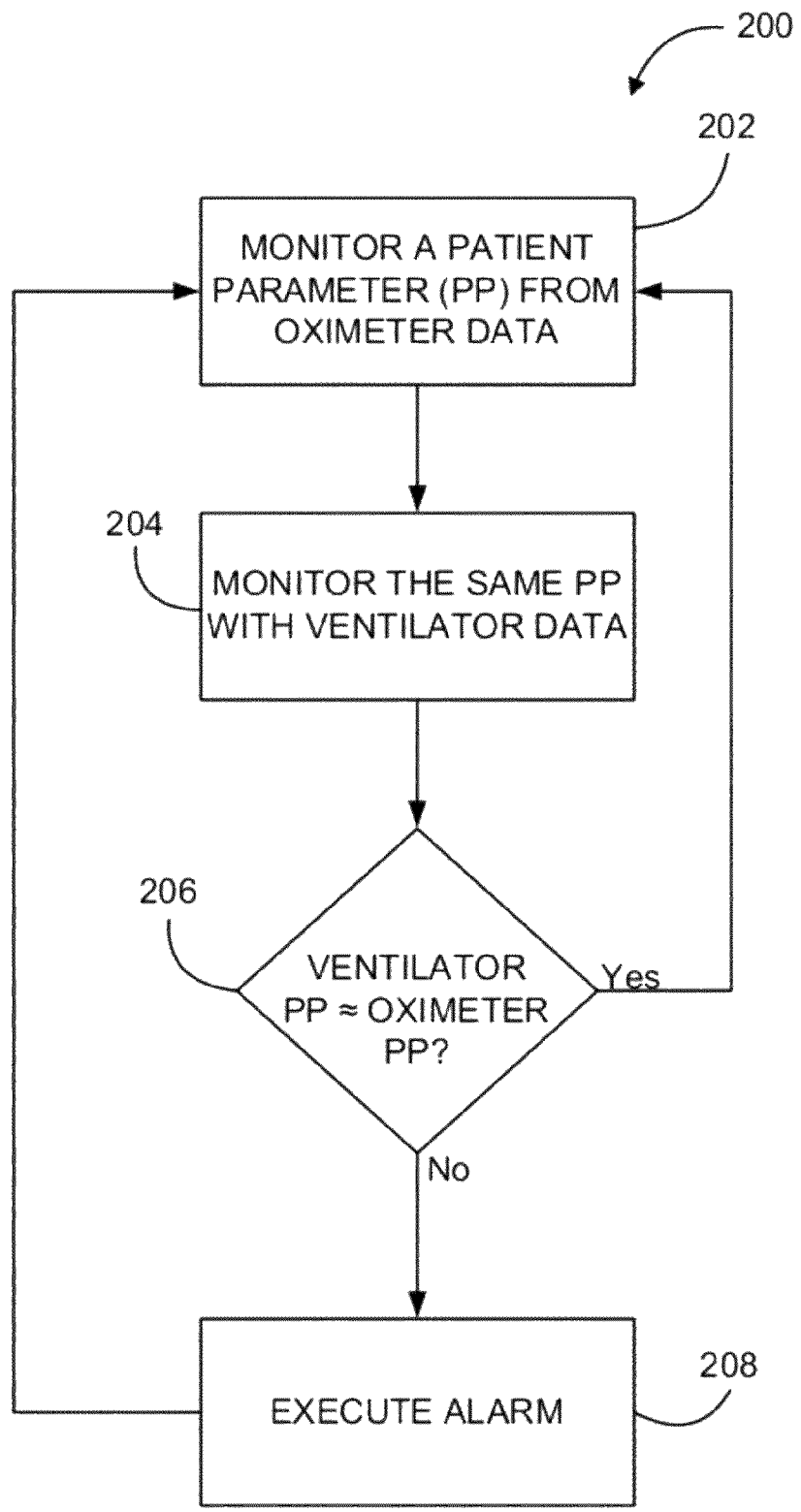
FIG. 2 illustrates an embodiment of a method for monitoring a patient being ventilated by a medical ventilator-oximeter system.

FIG. 2 illustrates an embodiment of a method for monitoring a patient being ventilated by a medical ventilator-oximeter system 200. As illustrated, method 200 performs a first monitoring operation 202. First monitoring operation 202 monitors a patient parameter (PP) for a patient attached to an oximeter sensor by utilizing oximeter data received from the oximeter sensor. In one embodiment, the patient parameter is at least one of respiration rate and pulse rate. In one embodiment, the pulse rate is monitored by using a photoplethysmogram from a light sensor. In another embodiment, the respiration rate is monitored by the oximeter using an embedded algorithm that processes frequency of changes in a magnitude of modulation (max-min) of an infrared plethysmorgram and/or baseline light level (a.k.a. the "DC" component).

Further, method 200 performs a second monitoring operation 204. Second monitoring operation 204 determines the same patient parameter as monitored by the first monitoring operation 202 by utilizing ventilator data from a patient attached to a ventilator independently of the oximeter data. In one embodiment, the data gathered by the ventilator is suitable for determining at least one of the pulse rate and/or respiration rate of the patient. In another embodiment, the pulse rate is monitored by the ventilator by detecting small pressure (flow) fluctuations in the breathing circuit under the influence of a contracting heart of the patient. In another embodiment, the respiration rate is monitored by the ventilator by using measured flow rates and/or pressures in the ventilator breathing circuit. In another embodiment, the respiration rate is monitored by using a preset, preselected, and/or preconfigured ventilator flow rate and/or a preset, preselected, and/or preconfigured ventilator respiration rate.

Next, method 200 performs a decision operation 206. Decision operation 206 compares the patient parameter monitored by using the oximeter data to the same patient parameter monitored by using the ventilator data and determines if the patient parameter monitored by the oximeter and the same patient parameter monitored by the ventilator differ by more than a predetermined value or are not substantially equivalent. If decision operation 206 determines that the patient parameter monitored by the oximeter and the same patient parameter monitored by the ventilator differ by more than a predetermined value, decision operation 206 selects to perform alarm operation 208. If decision operation 206 determines that patient parameter monitored by the oximeter and the same patient parameter monitored by the ventilator do not differ by more than a predetermined value or are substantially equivalent, decision operation 206 selects to perform the first monitoring operation 202.

The predetermined value is the greatest value that the two separately measured parameters can be different from each other if they were determined from sensor data measuring the same patient. A difference above the predetermined value is an indicator that the two separately determined parameters were most likely not determined from sensor measurements taken from the same patient. In one embodiment, the predetermined value is selected by an operator or inputted by an operator. In another embodiment the predetermined value is about 5% to about 10%. This range is not limiting. The predetermined value may vary depending upon the patient and the ventilator application. In one embodiment, the predetermined value is about 5%.

In one embodiment, decision operation 206 is performed upon user or operator command. In an alternative embodiment, decision operation 206 is performed at a preset, preselected, and/or preconfigured time. In another embodiment, decision operation 206 is performed continuously and/or repeatedly based on a preset, a preconfigured, and/or a preselected time duration.

Method 200 also performs alarm operation 208. Alarm operation 208 executes an alarm. The alarm may be an audio and/or visual warning. The visual warning may include flashing lights, a designated icon, or a simple worded notice on the display screen. This list is not limiting. Any suitable visual warning for notifying a ventilator-oximeter system operator that an oximeter sensor is potentially not attached to the same patient as the ventilator may be utilized by method 200.

The alarm alerts the operator that the oximeter sensor should be checked and if the oximeter sensor is not attached to the ventilator patient, the oximeter sensor should be placed on the ventilator patient. Accordingly, this alarm feature provides the operator of a ventilator-oximeter system with a check for verifying that the oximeter sensor of an oximeter is attached to the ventilator patient to prevent the ventilator and/or oximeter from displaying incorrect information. Further, the alarm provides the operator of the ventilator with a check for verifying that the oximeter and the ventilator are performing properly and/or not processing corrupted data. This check helps to prevent the operator from improperly treating a patient based on the improper information.

In one embodiment, method 200 further performs a disarming operation. The disarming operation disarms an executed alarm. In one embodiment, the disarming operation is performed upon operator command. In another embodiment, the disarming operation is executed after a predetermined, preselected, and preconfigured amount of alarm time.

Figure 3:
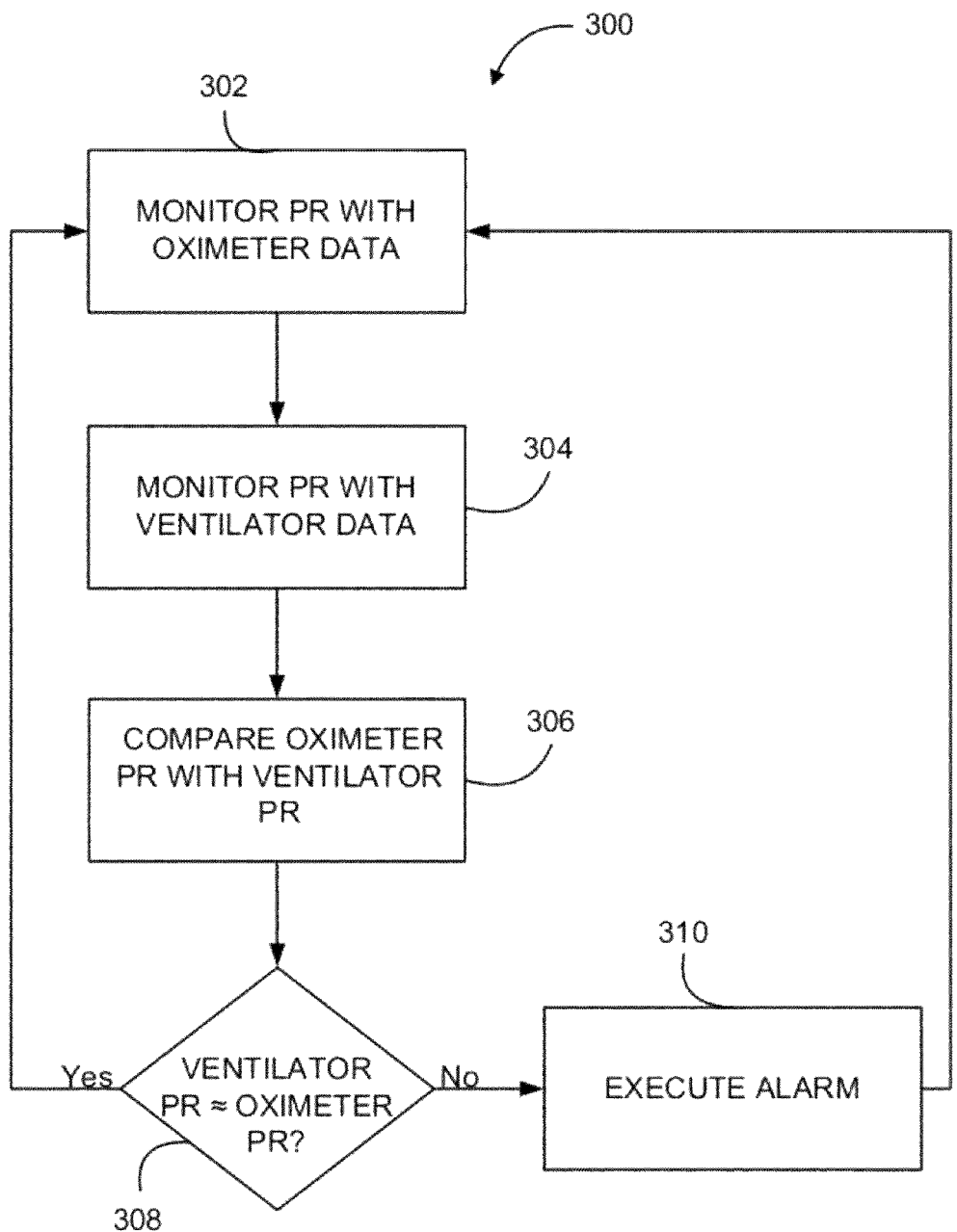
FIG. 3 illustrates an embodiment of a method for monitoring a patient being ventilated by a medical ventilator-oximeter system.

FIG. 3 illustrates an embodiment of a method for monitoring a patient being ventilated by a medical ventilator-oximeter system 300. As illustrated, method 300 performs a first pulse rate (PR) monitoring operation 302. First monitoring operation 302 monitors the pulse rate for a patient attached to an oximeter sensor by utilizing oximeter data gathered from the oximeter sensor. In one embodiment, the pulse rate is monitored using the photoplethysmogram from a light sensor.

Further, method 300 performs a second monitoring operation 304. Second monitoring operation 304 monitors the pulse rate for a patient by utilizing ventilator data gathered by a ventilator independently of the oximeter. In one embodiment, the pulse rate is monitored by the ventilator by detecting small pressure (flow) fluctuations in the breathing circuit under the influence of a contracting heart of the patient.

Method 300 also performs a compare operation 306. Compare operation 306 compares the pulse rate monitored by the oximeter to the pulse rate monitored by the ventilator. In an embodiment, compare operation 306 further compares the phase of the pulse rate monitored by the oximeter to the phase of the pulse rate monitored by the ventilator.

Next, method 300 performs a decision operation 308. Decision operation 308 determines if the pulse rate monitored by the oximeter and the pulse rate monitored by the ventilator differ by more than a predetermined value or are not substantially equivalent. If decision operation 308 determines that the pulse rate monitored by the oximeter and the pulse rate monitored by the ventilator differ by more than a predetermined value or are not substantially equivalent, decision operation 308 selects to perform alarm operation 310. If decision operation 308 determines that the pulse rate monitored by the oximeter and the pulse rate monitored by the ventilator do not differ by more than a predetermined value or are substantially equivalent, decision operation 308 selects to perform the first monitoring operation 302.

In one embodiment, when decision operation 308 determines that the pulse rate monitored by the oximeter and the pulse rate monitored by the ventilator do not differ by more than a predetermined value or are substantially equivalent, decision operation 308 selects to perform a phase decision operation. The phase decision operation determines if the phase of the pulse rate monitored by the oximeter and the phase of the pulse rate monitored by the ventilator differ by more than a predetermined value or are not substantially equivalent. If decision operation 308 determines that the phase of the pulse rate monitored by the oximeter and the phase of the pulse rate monitored by the ventilator differ by more than a predetermined value or are not substantially equivalent, decision operation 308 selects to perform alarm operation 310. If decision operation 308 determines that the phase of the pulse rate monitored by the oximeter and the phase of the pulse rate monitored by the ventilator do not differ by more than a predetermined value or are substantially equivalent, decision operation 308 selects to perform the first monitoring operation 302.

The predetermined value is the greatest value that the two separately monitored pulse rates can be different from each other if they were monitored using sensor data measuring the same patient. A pulse rate difference above the predetermined value is an indicator that the two separately monitored pulse rates were most likely not monitored using sensor readings taken from the same patient. In one embodiment, the predetermined value is selected by an operator or inputted by an operator. In another embodiment the predetermined value is about 5% to about 10%. This range is not limiting. The predetermined value may vary depending upon the patient and the ventilator application. In one embodiment, the predetermined value is about 5%.

In one embodiment, decision operation 308 and compare operation 306 are performed upon user or operator command. In an alternative embodiment, decision operation 308 and compare operation 306 are performed at a preset, preselected, and/or preconfigured time. In another embodiment, decision operation 308 and compare operation 306 are performed continuously and/or repeatedly.

Method 300 also performs an alarm operation 310. Alarm operation 310 executes an alarm. The alarm may be an audio and/or visual warning. The visual warning may include flashing lights, a designated icon, or a simple worded notice on the display screen. This list is not limiting. Any suitable visual warning for notifying a ventilator-oximeter system operator that an oximeter sensor is potentially not attached to the same patient as the ventilator may be utilized by method 300.

The alarm of method 300 notifies the operator that the oximeter sensor should be checked and if the oximeter sensor is not attached to the ventilator patient, the oximeter sensor should be placed on the ventilator patient. Accordingly, this alarm feature provides the operator of a ventilator-oximeter system with a check for verifying that the oximeter sensor of an oximeter is attached to the ventilator patient to prevent the ventilator and/or oximeter from displaying improper information. Further, the alarm provides the operator of the ventilator with a check for verifying that the oximeter and the ventilator are performing properly and/or not processing corrupted data. This check helps to prevent the operator from improperly treating a patient based on the improper information.

In one embodiment, method 300 further performs a disarming operation. The disarming operation disarms an executed alarm. In one embodiment, the disarming operation is performed upon operator command. In another embodiment, the disarming operation is executed after a predetermined, preselected, and/or preconfigured amount of alarm time.

Figure 4:
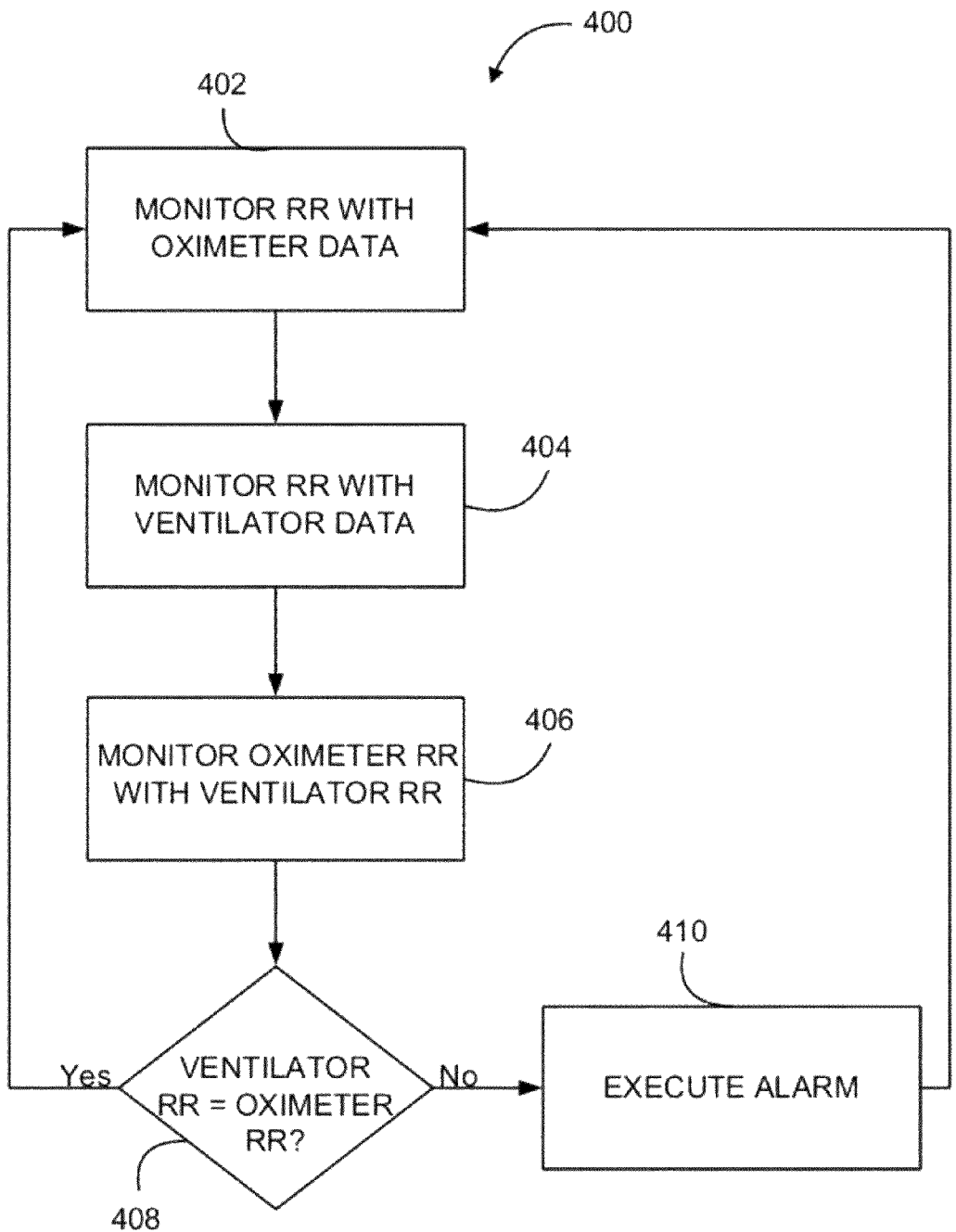
FIG. 4 illustrates an embodiment of a method for monitoring a patient being ventilated by a medical ventilator-oximeter system.

FIG. 4 illustrates an embodiment of a method for monitoring a patient being ventilated by a medical ventilator-oximeter system 400. As illustrated, method 400 performs a first monitoring operation 402. First monitoring operation 402 monitors a respiration rate (RR) for a patient attached to an oximeter sensor by utilizing oximeter data received from the oximeter sensor. In one embodiment, the respiration rate is monitored by the oximeter using an embedded algorithm that processes frequency of changes in a magnitude of modulation (max-min) of an infrared plethysmorgram and/or baseline light level (a.k.a. the "DC" component).

Further, method 400 performs a second monitoring operation 404. Second monitoring operation 404 monitors the respiration rate by utilizing ventilator data from a patient gathered by a ventilator independently of the oximeter. In one embodiment, the respiration rate is monitored by the ventilator by using a measured flow rate and/or pressure in the ventilator circuit. In another embodiment, the respiration rate is monitored by using a preset, a preconfigured, and/or a preselected flow rate, pressure rate, and/or respiration rate.

Method 400 also performs a compare operation 406. Compare operation 406 compares the respiration rate monitored by the oximeter to the respiration rate monitored by the ventilator. In an embodiment, compare operation 406 further compares a phase duration of the respiration rate monitored by the oximeter to the phase duration of the respiration rate monitored by the ventilator.

Next, method 400 performs a decision operation 408. Decision operation 408 determines if the respiration rate monitored by the oximeter and the respiration rate monitored by the ventilator differ by more than a predetermined value or are not substantially equivalent. If decision operation 408 determines that the respiration rate monitored by the oximeter and the respiration rate monitored by the ventilator data differ by more than a predetermined value or are not substantially equivalent, decision operation 408 selects to perform alarm operation 410. If decision operation 408 determines that the respiration rate monitored by the oximeter and the respiration rate monitored by the ventilator do not differ by more than a predetermined value or are substantially equivalent, decision operation 408 selects to perform first monitoring operation 402.

In one embodiment, when decision operation 408 determines that the respiration rate monitored by the oximeter and the respiration rate monitored by the ventilator do not differ by more than a predetermined value or are substantially equivalent, decision operation 408 selects to perform a phase decision operation. The phase decision operation determines if the phase duration of the respiration rate monitored by the oximeter and the phase duration of the respiration rate monitored by the ventilator differ by more than a predetermined value or are not substantially equivalent. If decision operation 408 determines that the phase duration of the respiration rate monitored by the oximeter and the phase duration of the respiration rate monitored by the ventilator differ by more than a predetermined value or are not substantially equivalent, decision operation 408 selects to perform alarm operation 410. If decision operation 408 determines that the phase duration of the respiration rate monitored by the oximeter and the phase duration of the respiration rate monitored by the ventilator do not differ by more than a predetermined value or are substantially equivalent, decision operation 408 selects to perform the first monitoring operation 402.

The predetermined value is the greatest value that the two separately determined respiration rates can be different from each other if they were determined from sensor data measuring the same patient. A respiration rate difference above the predetermined value is an indicator that the two separately measured values were most likely not taken from the same patient. In one embodiment, the predetermined value is selected by an operator or inputted by an operator. In another embodiment the predetermined value is about 5% to about 10%. This range is not limiting. The predetermined value may vary depending upon the patient and the ventilator application. In one embodiment, the predetermined value is about 5%.

In one embodiment, decision operation 408 and compare operation 406 are performed upon user or operator command. In an alternative embodiment, decision operation 408 and compare operation 406 are performed at a preset, preselected, or preconfigured time. In another embodiment, decision operation 408 and compare operation 406 are performed continuously and/or repeatedly.

Method 400 also performs an alarm operation 410. Alarm operation 410 executes an alarm. The alarm may be an audio and/or visual warning. The visual warning may include flashing lights, a designated icon, or a simple worded notice on the display screen. This list is not limiting. Any suitable visual warning for notifying a ventilator-oximeter system operator that an oximeter sensor is potentially not attached to the same patient as the ventilator may be utilized by method 400.

The alarm notifies the operator that the oximeter sensor should be checked and if the oximeter sensor is not attached to the ventilator patient, the oximeter sensor should be placed on the ventilator patient. Accordingly, this alarm feature provides the operator of a ventilator-oximeter system with a check for verifying that the oximeter sensor of an oximeter is attached to the ventilator patient to prevent the ventilator and/or oximeter from displaying improper information. Further, the alarm provides the operator of the ventilator with a check for verifying that the oximeter and the ventilator are performing properly and/or not processing corrupted data. This check helps to prevent the operator from improperly treating a patient based on the improper information.

In one embodiment, method 400 further performs a disarming operation. The disarming operation disarms an executed alarm. In one embodiment, the disarming operation is performed upon operator command. In another embodiment, the disarming operation is executed after a predetermined, preselected, and preconfigured amount of alarm time.

Figure 5:
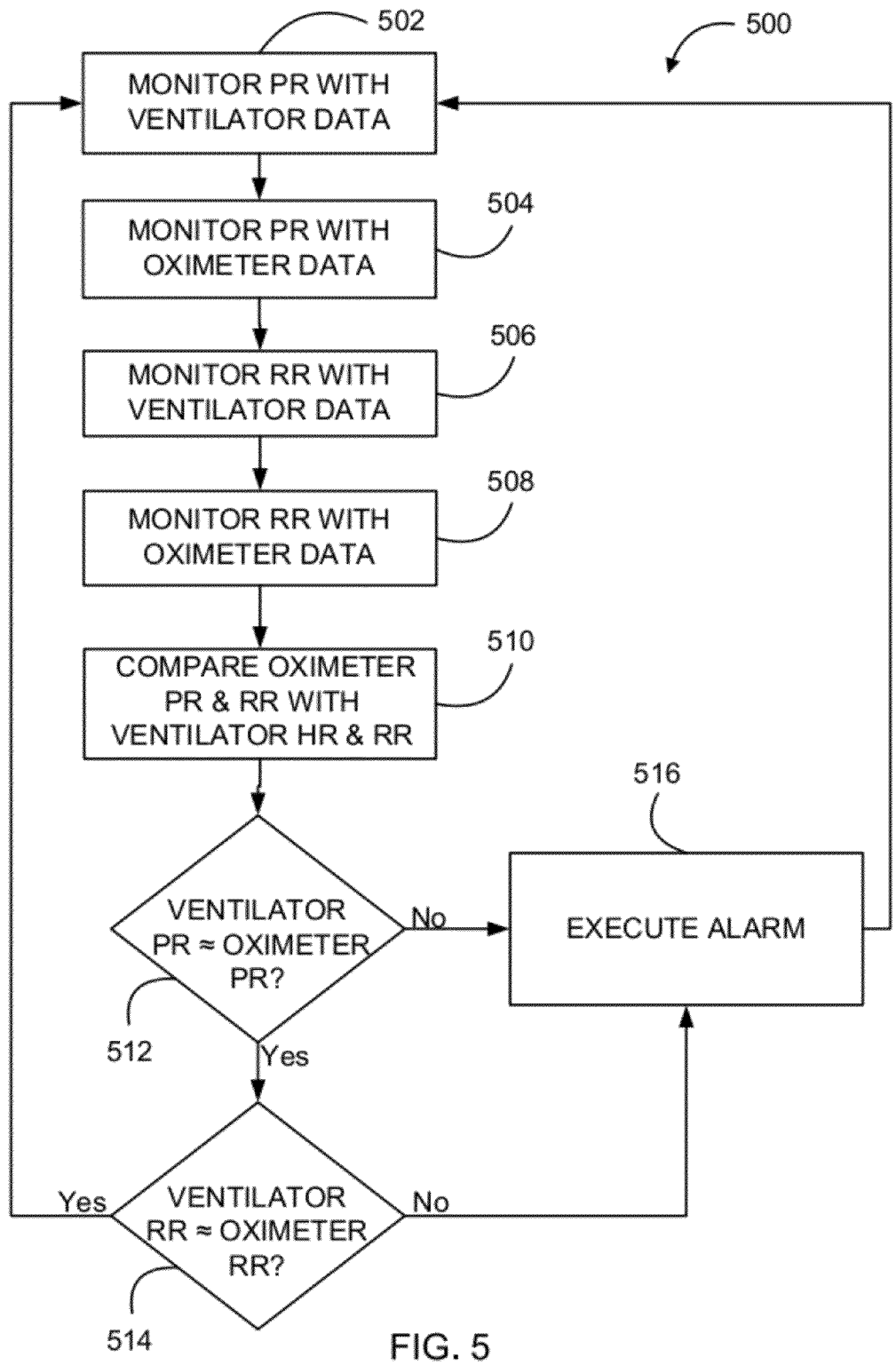
FIG. 5 illustrates an embodiment of a method for monitoring a patient being ventilated by a medical ventilator-oximeter system.

As illustrated in FIG. 5, in one embodiment, methods 300 and 400 are performed in combination 500. Method 500 performs a first PR monitoring operation 502, a first RR monitoring operation 506, a second PR monitoring operation 504, a second RR monitoring operation 508, a compare operation 510, a PR decision operation 512, a RR decision operation 514, and an alarm operation 516. First monitoring operations 502 and 506 are identical to first monitoring operations 304 and 404 as described above. Second monitoring operations 504 and 508 are identical to second monitoring operations 302 and 402 as described above. Compare operation 510 is identical to the combination of compare operations 306 and 406 as described above. Alarm operation 516 is identical to the alarm operations 410 and 310 as described above.

PR decision operation 512 determines if the pulse rate monitored by the oximeter and the pulse rate monitored by ventilator differ by more than a predetermined value or are not substantially equivalent. RR decision operation 514 determines if the respiration rate monitored by the oximeter and the respiration rate monitored by ventilator differ by more than a predetermined value or are not substantially equivalent.

Decision operations 512 and 514 may be performed in any order. Decision operation 512 may be performed before decision operation 514 or decision operation 514 may be performed before decision operation 512. If either decision operation 512 or 514 determine that the pulse rate and/or respiration rate monitored by the oximeter and the pulse rate and/or respiration rate monitored by the ventilator differ by more than a predetermined value or are not substantially equivalent, decision operations 512 and 514 select to perform alarm operation 516.

If the decision operation 512 is performed before decision operation 514 and decision operation 512 determines that the pulse rate monitored by the oximeter and the pulse rate monitored by the ventilator do not differ by more than a predetermined value or are substantially equivalent, decision operation 512 selects to perform decision operation 514. If the decision operation 512 is performed after decision operation 514 and decision operation 512 determines that the pulse rate monitored by the oximeter and the pulse rate monitored by the ventilator do not differ by more than a predetermined value or are substantially equivalent, decision operation 512 selects to perform first PR monitoring operation 502.

If the decision operation 514 is performed before decision operation 512 and decision operation 514 determines that the respiration rate monitored by the oximeter and the respiration rate monitored by the ventilator do not differ by more than a predetermined value or are substantially equivalent, decision operation 514 selects to perform decision operation 512. If the decision operation 514 is performed after decision operation 512 and decision operation 514 determines that the respiration rate monitored by the oximeter and the respiration rate monitored by the ventilator do not differ by more than a predetermined value or are substantially equivalent, decision operation 514 selects to perform first PR monitoring operation 502.

In an alternative embodiment, not illustrated, method 500 requires both decision operations 512 and 514 to determine that their parameters (i.e. pulse rate and respiration rate) differ by more than a predetermined value or are not substantially equivalent before performing alarm operation 516.

In another embodiment, method 500 selects to further perform a disarming operation. The disarming operation is identical to disarming operations described above for methods 200, 300, and 400.

Figure 6:
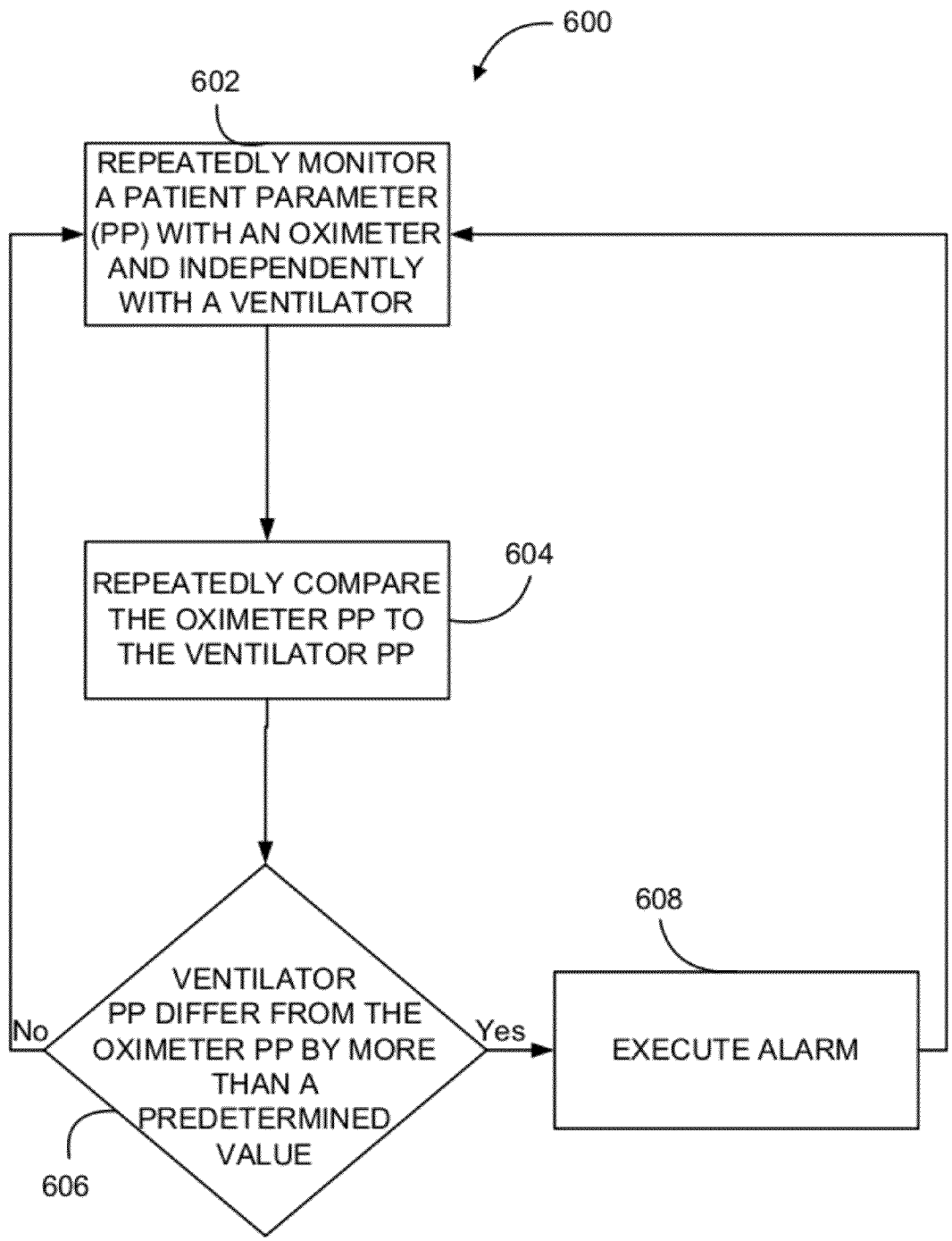
FIG. 6 illustrates an embodiment of a computer-readable medium having computer-executable instructions for performing a method for monitoring a patient being ventilated by a medical ventilator-oximeter system.

As illustrated in FIG. 6, in one embodiment, a computer-readable medium having computer-executable instructions for performing a method 600 for monitoring a patient being ventilated by a medical ventilator-oximeter system is shown.

Method 600 performs a monitoring operation 602. The monitoring operation 602 repeatedly monitors at least one patient parameter with an oximeter and with a ventilator independently of the oximeter.

Further, method 600 performs a compare operation 604. Compare operation 604 repeatedly compares the at least one patient parameter monitored by the oximeter to the at least one patient parameter monitored by the ventilator.

Method 600 also performs a determination operation 606. Determination operation 606 determines if the at least one patient parameter monitored by the oximeter differs from the at least one parameter monitored by the ventilator by more than a predetermined value. If the at least one patient parameter monitored by the oximeter differs from the at least one parameter monitored by the ventilator by more than a predetermined value, method 600 performs alarm execution operation 608. If the at least one patient parameter monitored by the oximeter does not differ from the at least one parameter monitored by the ventilator by more than a predetermined value, method 600 performs monitoring operation 602 again, Next method 600 performs an alarm execution operation 608. The alarm execution operation 608 executes an alarm after the step of determining that the at least one patient parameter monitored by the oximeter differs from the at least one parameter monitored by the ventilator by more than a predetermined value.

Example 1

Numerous other changes may be made which will readily suggest themselves to those skilled in the art and which are encompassed in the spirit of the disclosure and as defined in the appended claims. While various embodiments have been described herein for purposes of this disclosure, various changes and modifications may be made which are well within the scope of the present invention. Numerous other changes may be made which will readily suggest themselves to those skilled in the art and which are encompassed in the spirit of the disclosure and as defined in the claims.

What is claimed is:

1. A method for monitoring a patient being ventilated by a medical ventilator-oximeter system, the method comprising:
    monitoring at least one patient parameter using data gathered by an oximeter;
    monitoring the same at least one patient parameter using data gathered by a ventilator independently of the oximeter;
    comparing the at least one patient parameter monitored by the oximeter to the same at least one patient parameter monitored by the ventilator; and
    executing an alarm to notify an operator of the medical ventilator-oximeter system that an oximeter sensor is not attached to the patient being ventilated by the ventilator when the at least one patient parameter monitored by the oximeter and the ventilator differ by more than a predetermined value.

2. The method of claim 1, wherein the at least one patient parameter monitored by the oximeter and the ventilator is at least one of respiration rate and pulse rate.

3. The method of claim 2, wherein the respiration rate and the pulse rate include related phase information.

4. The method of claim 1, wherein the at least one patient parameter is a pulse rate and wherein the pulse rate is monitored by the ventilator by detecting small pressure (flow) fluctuations in a breathing circuit under an influence of a contracting heart of the patient.

5. The method of claim 1, wherein the at least one patient parameter is respiration rate and wherein the respiration rate is monitored by the oximeter using an embedded algorithm that processes frequency of changes in a magnitude of modulation (max-min) of an infrared plethysmorgram.

6. The method of claim 1, wherein the alarm is at least one of audio and visual.

7. The method of claim 1, where in the comparing step is performed upon an operator command.

8. The method of claim 1, further comprising, disarming the alarm upon an operator command.

9. The method of claim 1, wherein the predetermined value is 5 percent.

10. A method for monitoring a patient being ventilated by a medical ventilator-oximeter system, the method comprising:

monitoring a pulse rate of a patient using data gathered by an oximeter;

monitoring the pulse rate of the patient using data gathered by a ventilator independently of the oximeter;

comparing the pulse rate monitored by the oximeter to the pulse rate monitored by the ventilator; and executing an alarm to notify an operator of the medical ventilator-oximeter system that an oximeter sensor is not attached to the patient being ventilated by the ventilator when the pulse rate monitored by the oximeter and the pulse rate monitored by the ventilator differ by more than a predetermined value.

11. The method of claim 10, further comprising:

monitoring a respiration rate of the patient using data gathered by the oximeter;

monitoring the respiration rate of the patient using data gathered by the ventilator independently of the oximeter; and comparing the respiration rate monitored by the oximeter to the respiration rate monitored by the ventilator;

wherein the step of executing the alarm further comprises executing the alarm to notify the operator of the medical ventilator-oximeter system that the oximeter sensor is not attached to the patient being ventilated by the ventilator when the pulse rate and the respiration rate monitored by the oximeter and the pulse rate and the respiration rate monitored by the ventilator differ by more than the predetermined value.

12. The method of claim 11, further comprising:

determining that the difference in the pulse rate is about equal to the difference in the respiration rate.

13. The method of claim 11, wherein the respiration rate is monitored by the oximeter using an embedded algorithm that processes frequency of changes in a magnitude of modulation (max-min) of a baseline of an infrared plethysmorgram.

14. The method of claim 10, wherein the predetermined value is 5 percent.

15. The method of claim 10, wherein the comparing step and the monitoring steps are performed upon an operator command.

16. The method of claim 10, further comprising, disarming the alarm upon an operator command.

17. The method of claim 10, wherein the pulse rate is monitored by the ventilator by detecting small pressure (flow) fluctuations in a breathing circuit under an influence of a contracting heart of the patient.

18. A method for monitoring a patient being ventilated by a medical ventilator-oximeter system, the method comprising:

monitoring a respiration rate of a patient using data gathered from an oximeter;

monitoring the respiration rate of the patient using data gathered by a ventilator independently of the oximeter;

comparing the respiration rate monitored by the oximeter to the respiration rate monitored by the ventilator; and executing an alarm to notify an operator of the medical ventilator-oximeter system that an oximeter sensor is not attached to the patient being ventilated by the ventilator when the respiration rate monitored by the oximeter and the respiration rate monitored by the ventilator differ by more than a predetermined value.

19. The method of claim 18, wherein the predetermined value is 5 percent.

20. A medical ventilator-oximeter system, comprising:

a ventilator, the ventilator comprising a processor, a pneumatic gas delivery system controlled by the processor, the pneumatic gas delivery system adapted to control a flow of gas from a gas supply to a patient via a ventilator breathing circuit, at least one sensor in communication with the processor, data from the at least one sensor is utilized to determine a respiration rate of the patient, and a cardiac oscillation detector in communication with the processor, data from the cardiac oscillation detector is utilized to determine a pulse rate of the patient;

an oximeter operatively coupled to the ventilator, comprising, an oximeter sensor in communication with the processor, a pulse rate module in communication with the processor, and an infrared plethysmorgram module in communication with the processor;

a comparing module, the comparing module compares at least one patient parameter monitored by using oximeter data to the same at least one patient parameter monitored independently by using ventilator data;

an alarm module, the alarm module executes an alarm when the at least one patient parameter monitored by using the oximeter data and the same at least one patient parameter monitored by using the ventilator data differ by more than a predetermined value; and a display module controlled by the processor, the display module is adapted to display an executed alarm.

21. The medical ventilator-oximeter system of claim 20, wherein the compared at least one patient parameter monitored using the oximeter data and the ventilator data is at least one of respiration rate and the pulse rate.

22. A non-transitory computer-readable medium having computer-executable instructions executed by a processor of a controller for monitoring a patient being ventilated by a medical ventilator-oximeter system, the controller comprising:

a compare module that repeatedly monitors at least one patient parameter with an oximeter and with a ventilator independently of the oximeter and repeatedly compares the at least one patient parameter monitored by the oximeter to the at least one patient parameter monitored by the ventilator; and an alarm module that determines that the at least one patient parameter monitored by the oximeter differs from the at least one patient parameter monitored by the ventilator by more than a predetermined value and executes an alarm after the step of determining that the at least one patient parameter monitored by the oximeter differs from the at least one patient parameter monitored by the ventilator by more than the predetermined value.

23. A medical ventilator-oximeter system, comprising:

means for repeatedly monitoring at least one patient parameter with an oximeter and with a ventilator independently of the oximeter;

means for repeatedly comparing the at least one patient parameter monitored by the oximeter to the at least one patient parameter monitored by the ventilator;

means for determining that the at least one patient parameter monitored by the oximeter differs from the at least one patient parameter monitored by the ventilator by more than a predetermined value; and means for executing an alarm after the step of determining that the at least one patient parameter monitored by the oximeter differs from the at least one patient parameter monitored by the ventilator by more than the predetermined value.

* * * * *